United States Patent
Chakravorty et al.

(10) Patent No.: US 9,943,225 B1
(45) Date of Patent: Apr. 17, 2018

(54) EARLY PREDICTION OF AGE RELATED MACULAR DEGENERATION BY IMAGE RECONSTRUCTION

(71) Applicant: International Business Machines Corporation, Armonk, NY (US)

(72) Inventors: Rajib Chakravorty, Epping (AU); Rahil Garnavi, Macleod (AU); Dwarikanath Mahapatra, Melbourne (AU); Pallab Roy, Melbourne (AU); Suman Sedai, Melbourne (AU)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/273,963

(22) Filed: Sep. 23, 2016

(51) Int. Cl.
*A61B 3/00* (2006.01)
*A61B 3/10* (2006.01)
(Continued)

(52) U.S. Cl.
CPC ........... *A61B 3/0025* (2013.01); *A61B 3/102* (2013.01); *A61B 3/1225* (2013.01);
(Continued)

(58) Field of Classification Search
CPC ....... A61B 3/005; A61B 3/102; A61B 3/1225; A61B 5/7275; G06K 9/0061; G06K 9/00617; G06K 9/6215; G06K 2209/05
See application file for complete search history.

(56) References Cited

U.S. PATENT DOCUMENTS

| 9,119,562 B2 * | 9/2015 | Naba ................... A61B 3/1025 |
| 2011/0176716 A1 * | 7/2011 | Kim ...................... G06T 3/0075 382/131 |

(Continued)

FOREIGN PATENT DOCUMENTS

| JP | 2006061196 A | * | 3/2006 | |
| WO | WO 2010140476 A1 | * | 12/2010 | ........... G06T 7/0012 |

OTHER PUBLICATIONS

Hu et al., Multimodel Retinal Vessel Segmentation From Spectral-Domain Optical Coherence Tomography and Fundus Photography, IEEE Transactions on Medical Imaging, vol. 31, No. 10, pp. 1900-1911, Oct. 2012.*

(Continued)

*Primary Examiner* — Brenda Bernardi
(74) *Attorney, Agent, or Firm* — Harrington & Smith; Louis J. Percello

(57) ABSTRACT

An AMD prediction model utilizes an OCT image estimation model. The OCT image estimation module is created by segmenting an OCT image to generate an OCT projection image for each of multiple biological layers; extracting from each of the generated OCT projection images a first set of features; extracting a second set of features from an input retinal fundus image; for each respective biological layer, registering the input retinal fundus image to the respective OCT projection image by matching at least some of the second set of features with corresponding ones of the first set of features; repeating the above with changes to the input retinal fundus image; and modelling how the changes to the input retinal fundus image are manifest at the correspondingly registered projection images. Estimated OCT projection images can then be generated for the multiple biological layers from a given retinal fundus image.

20 Claims, 16 Drawing Sheets

(51) Int. Cl.
*A61B 3/12* (2006.01)
*A61B 5/00* (2006.01)
*G06K 9/00* (2006.01)
*G06K 9/62* (2006.01)

(52) U.S. Cl.
CPC .......... *A61B 5/7275* (2013.01); *G06K 9/0061* (2013.01); *G06K 9/00617* (2013.01); *G06K 9/6215* (2013.01); *G06K 2209/05* (2013.01)

(56) References Cited

U.S. PATENT DOCUMENTS

| | | | |
|---|---|---|---|
| 2017/0112372 A1* | 4/2017 | Chakravorty | A61B 3/0025 |
| 2017/0119247 A1* | 5/2017 | Walsh | A61B 3/102 |
| 2017/0231492 A1* | 8/2017 | Sudo | A61B 3/0091 351/206 |
| 2017/0270653 A1* | 9/2017 | Garnavi | G06T 7/0002 |
| 2017/0273557 A1* | 9/2017 | Nakazawa | A61B 3/1225 |
| 2017/0273558 A1* | 9/2017 | Tamura | A61B 3/14 |

OTHER PUBLICATIONS

Gorczynska, Iwona, et al. "Projection OCT fundus imaging for visualising outer retinal pathology in non-exudative age-related macular degeneration." [British Journal of Ophthalmology 93.5 (2009): 603-609].

Kandel, Benjamin M., et al. "Predicting cognitive data from medical images using sparse linear regression." [Information Processing in Medical Imaging; Springer. Berlin, Heidelberg, (2013).] proposes a sparse linear regression model to estimate cognitive data from Magnetic Resonance Imaging (MRI).

Yang, Jimei, et al. "Weakly-supervised disentangling with recurrent transformations for 3d view synthesis." [Advances in Neural Information Processing Systems. (2015)] proposes a recurrent convolutional encoder-decoder network to synthesize novel views of a 3D object from a single image.

Fischer, Philipp, et al. "FlowNet: Learning Optical Flow with Convolutional Networks." [ARXIV Preprint ARXIV:1504.06852 (2015)] presents two architecture of convolutional neural network for estimating optical flows—one architecture is the generic architecture and other uses a specific layer that correlates feature vectors at different image locations.

Gregor, Karol, et al. "DRAW: A recurrent neural network for image generation." [ARXIV Preprint ARXIV: 1502.04623 (2015)] describes a Deep Recurrent Attentive Writer (DRAW) neural network architecture for image generation. DRAW networks combine a spatial attention mechanism that mimics the foveation of the human eye, with a sequential variational auto-encoding framework that allows for the iterative construction of complex images to yield a deep convolutional neural network based auto-encoder.

Masci, Jonathan, et al. "Stacked convolutional auto-encoders for hierarchical feature extraction." [Artificial Neural Networks and Machine Learning—ICANN 2011, p. 52-59. Springer. Berlin, Heidelberg (2011)].

Stacked Denoising Autoencoders: Learning Useful Representations in a Deep Network with a Local Denoising Criterion [Vincent (2010)].

Contractive Auto-Encoders: Explicit Invariance During Feature Extraction [Rifai (2011)].

Vecino, Elena, et al. "Glia—neuron interactions in the mammalian retina." [Progress in Retinal and Eye Research (2015)].

Nowak, Eric, Frédéric Jun., and Bill Triggs. "Sampling strategies for bag-of-features image classification." [Computer Vision—ECCV 2006, p. 490-503. Springer. Berlin, Heidelberg (2006)].

* cited by examiner

EARLY PREDICTION OF AGE RELATED MACULAR DEGENERATION BY IMAGE RECONSTRUCTION

TECHNICAL FIELD

The exemplary embodiments of this invention relate generally to predicting age related macular degeneration (AMD) using a patient's color retinal fundus image as an input, and more particularly is directed towards generating estimated optical coherence tomography (OCT) projection images from only a retinal fundus image from which the AMD prediction can be accurately made.

BACKGROUND

Age related macular degeneration (AMD) is a leading cause of blindness. More specifically, AMD) is a medical condition usually affecting older adults that results in vision loss in the center of the visual field (the macula) because of damage to the retina. AMD is a major cause of visual impairment in older adults (>50 years). Macular degeneration can make it difficult or impossible to read or recognize faces, though often there remains enough peripheral vision to allow other activities of daily life.

FIG. 1 is a schematic drawing of the cellular components of the retina showing the glia and neurons. The different cell types are situated in a standard large mammalian retina and are designated in FIG. 1 using the following abbreviations: amacrine cells (A), astrocytes (AS), bipolar cells (B), cones (C), ganglion cells (G), horizontal cells (H), Müller cells (M), microglia (Mi), rods (R), and cones (C). Note the interactions between the cells and blood vessels (BV). Note also the location of the different layers of the retina from the most internal to the outermost layers: the innermost optic nerve (ON), nerve fibre layer (NFL), ganglion cell layer (GCL), inner plexiform layer (IPL), inner nuclear layer (INL), outer plexiform layer (OPL), outer nuclear layer (ONL), outer segment layer (OS), pigment epithelium (PE), and the outermost choroid (Ch). [FIG. 1 is reproduced from Vecino, Elena, et al. "Glia-neuron interactions in the mammalian retina." [*Progress in retinal and eye research* (2015)].

The inner layer of the eye is the retina and comprises a number of layers. Behind the retina is the choroid which contains the blood supply to all three layers of the eye, including the macula which is the central part of the retina that surrounds the optic disc. AMD occurs in "dry" and "wet" forms. In the dry (nonexudative) form, cellular debris called drusen accumulates between the retina and the choroid, and the retina can become detached. In the wet (exudative) form which are more severe, blood vessels grow up from the choroid behind the retina, and the retina can become detached. It can be treated with laser coagulation, and with medication that stops and sometimes reverses the growth of blood vessels.

Early detection and prediction of AMD can reduce the incidence of blindness. Pathological changes in different retinal tissue layers (such as drusens, retinal pigment epithelium (RPE) abnormalities, etc.) are the indication of early stages of AMD. Retinal imaging is mainly used for the diagnosis of AMD, and has evolved rapidly during the last 160 years to the extent it is now widely used for clinical care and management of patients with retinal as well as systemic diseases. Retinal fundus photography and optical coherence tomography (OCT) are the leading retinal imaging technologies in current use.

Retinal fundus photography is defined as the process whereby a two-dimensional (2-D) representation of the three-dimensional (3-D) retinal semi-transparent tissues projected onto the imaging plane is obtained by using reflected light. Optical coherence tomography (OCT) is an established medical imaging technique that uses light to capture high resolution and three-dimensional images of optical scattering media (for example, the retina). Optical coherence tomography is based on low-coherence interferometry, typically employing near-infrared light. The use of relatively long wavelength light allows it to penetrate into the scattering medium.

Projection optical coherence tomography (OCT) fundus images can provide enhanced visualization of different retinal layers which is very useful for the early prediction of AMD [(see Gorczynska, Iwona, et al. in the reference listing below). Projection OCT fundus images are generated from ultrahigh-resolution OCT images. But ultrahigh resolution OCT imaging technology is very expensive and not available in many remote and rural areas. Embodiments of these teachings provide a more cost-effective technique to predict AMID than OCT imaging.

In this regard the following references are relevant:

Gorczynska, Iwona, et al. "*Projection OCT fundus imaging for visualising outer retinal pathology in non-exudative age-related macular degeneration.*" [BRITISH JOURNAL OF OPHTHALMOLOGY 93.5 (2009): 603-609].

Kandel, Benjamin M., et al. "*Predicting cognitive data from medical images using sparse linear regression.*" [INFORMATION PROCESSING IN MEDICAL IMAGING; Springer. Berlin, Heidelberg, (2013).] proposes a sparse linear regression model to estimate cognitive data from Magnetic Resonance Imaging (MRI).

Yang, Jimei, et al. "*Weakly-supervised disentangling with recurrent transformations for 3d view synthesis.*" [ADVANCES IN NEURAL INFORMATION PROCESSING SYSTEMS. (2015)] proposes a recurrent convolutional encoder-decoder network to synthesize novel views of a 3D object from a single image.

Fischer, Philipp, et al. "*FlowNet: Learning Optical Flow with Convolutional Networks.*" [ARXIV PREPRINT ARXIV: 1504.06852 (2015)] presents two architecture of convolutional neural network for estimating optical flows—one architecture is the generic architecture and other uses a specific layer that correlates feature vectors at different image locations.

Gregor, Karol, et al. "*DRAW: A recurrent neural network for image generation.*" [ARXIV PREPRINT ARXIV: 1502.04623 (2015)] describes a Deep Recurrent Attentive Writer (DRAW) neural network architecture for image generation. DRAW networks combine a spatial attention mechanism that mimics the foveation of the human eye, with a sequential variational auto-encoding framework that allows for the iterative construction of complex images to yield a deep convolutional neural network based autoencoder.

Masci, Jonathan, et al. "*Stacked convolutional auto-encoders for hierarchical feature extraction.*" [ARTIFICIAL NEURAL NETWORKS AND MACHINE LEARNING-ICANN 2011, p 52-59. Springer. Berlin, Heidelberg (2011)].

*Stacked Denoising Autoencoders: Learning Useful Representations in a Deep Network with a Local Denoising Criterion* [Vincent (2010)].

*Contractive Auto-Encoders: Explicit Invariance During Feature Extraction* [Rifai (2011)].

*Stacked Convolutional Auto-Encoders for Hierarchical Feature Extraction* [J. Masci (2011)].

Vecino, Elena, et al. "*Glia-neuron interactions in the mammalian retina.*" [PROGRESS IN RETINAL AND EYE RESEARCH (2015)].

Nowak, Eric, Frédéric Jurie, and Bill Triggs. "*Sampling strategies for bag-of-features image classification.*" [COMPUTER VISION-ECCV 2006, page 490-503. Springer. Berlin, Heidelberg (2006)].

SUMMARY

In a first aspect thereof the embodiments of this invention provide a method comprising:
 a. segmenting an optical coherence tomography (OCT) image to generate an OCT projection image for each of multiple biological layers;
 b. extracting from each of the generated OCT projection images a first set of features;
 c. extracting a second set of features from an input retinal fundus image;
 d. for each respective biological layer, registering the input retinal fundus image to the respective OCT projection image by matching at least some of the second set of features with corresponding ones of the first set of features;
 e. repeating elements a) through d) with changes to the input retinal fundus image;
 f. modelling how the changes to the input retinal fundus image are manifest at the correspondingly registered projection images; and
 g. storing in a computer readable memory a program that utilizes the modelling to generate estimated OCT projection images for the multiple biological layers from a given retinal fundus image.

In a second aspect of this invention there is a computer readable memory storing an executable program comprising:
 a. code to segment an optical coherence tomography (OCT) image to generate an OCT projection image for each of multiple biological layers;
 b. code to extract from each of the generated OCT projection images a first set of features;
 c. code to extract a second set of features from an input retinal fundus image;
 d. code to register the input retinal fundus image to the respective OCT projection images of each respective biological layer by matching at least some of the second set of features with corresponding ones of the first set of features;
 e. code to repeat elements a) through d) with changes to the input retinal fundus image;
 f. code to model how the changes to the input retinal fundus image are manifest at the correspondingly registered projection images; and
 g. code to utilize the model for generating estimated OCT projection images for the multiple biological layers from a given retinal fundus image.

In a third aspect of this invention there is an apparatus comprising: one or more memories comprising computer-readable code and one or more processors, wherein the one or more processors are configured, in response to execution of the computer-readable code, to cause the apparatus to perform actions comprising:
 a. segmenting an optical coherence tomography (OCT) image to generate an OCT projection image for each of multiple biological layers;
 b. extracting from each of the generated OCT projection images a first set of features;
 c. extracting a second set of features from an input retinal fundus image;
 d. for each respective biological layer, registering the input retinal fundus image to the respective OCT projection image by matching at least some of the second set of features with corresponding ones of the first set of features;
 e. repeating elements a) through d) with changes to the input retinal fundus image;
 f. modelling how the changes to the input retinal fundus image are manifest at the correspondingly registered projection images; and
 g. storing in the one or more memories a program that utilizes the modelling to generate estimated OCT projection images for the multiple biological layers from a given retinal fundus image.

These and other aspects are detailed below with further particularity.

DETAILED DESCRIPTION

OCT imaging can effectively predict AMD because OCT imaging allows us to obtain retinal tissue layer-specific information that directly correlates to (predicts) AMD. Retinal fundus tissue images cannot give us that layer-specific information and so lacks that predictive power, or at least that was the case prior to these teachings. While OCT imaging is expensive and not yet widely available in rural and remote regions, retinal color fundus images are relatively inexpensive and much more widely available. Embodiments of these teachings exploit the high correlation in changes in retinal fundus images over time with changes in the projection OCT fundus images of different tissue layers. As will be further detailed below, these teachings provide a model by which to estimate the projection optical coherence tomography (OCT) fundus images of different retinal tissue layers from retinal color fundus images. The combination of estimated projection OCT images of different retinal tissue layers and retinal color fundus image can further be used in a machine learning pipeline for the early prediction of AMD.

Figure 1:
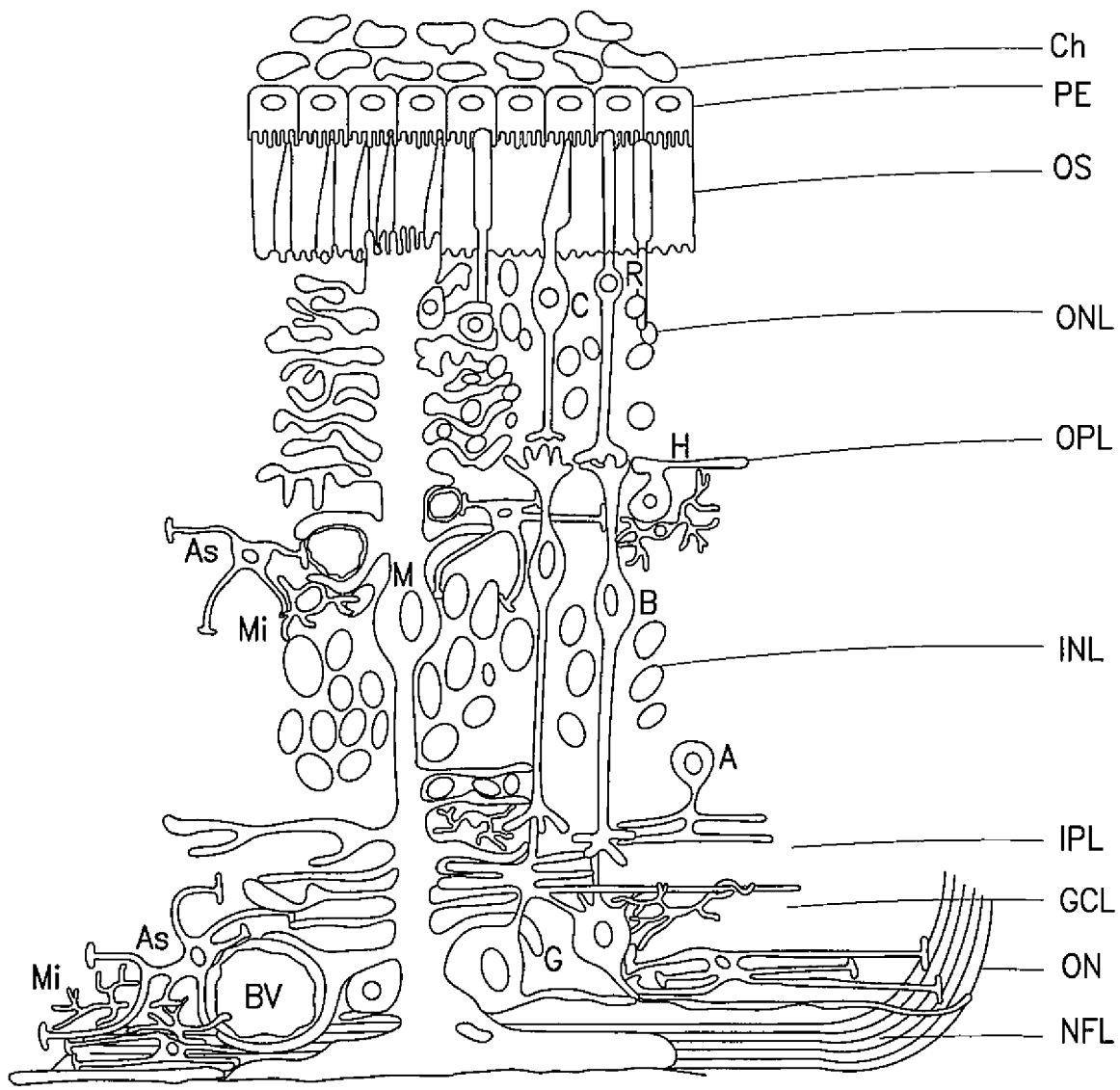
FIG. 1 is a prior art schematic drawing of the cellular components of the retina.
Figure 2:
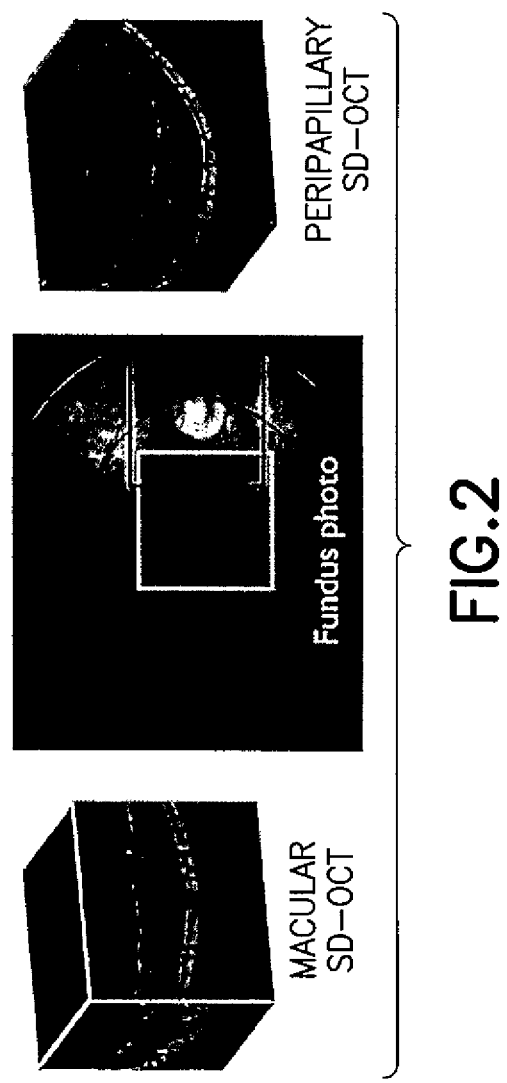
FIG. 2 illustrate two common locations of spectral domain OCT images illustrated on a central fundus photo, and OCT volumetric scans of those locations.

The central portion of FIG. 2 illustrates a retinal fundus image with the macula region delineated by the central rectangle and the optic disc region delineated by the offset rectangle. The left side of FIG. 2 shows a corresponding OCT volumetric image centered on the macula while the right side of FIG. 2 is a corresponding OCT volumetric image centered on the optic nerve head region. Recent advancement in OCT imaging technology enables us to capture these ultrahigh-resolution three dimensional optical coherence tomography (3D-OCT) shown at the left and right sides of FIG. 2. Such 3D-OCT images may be used to generate projection OCT fundus images as will be shown for FIG. 3 by selectively summing different retinal depth levels.

Figure 3C:
FIGS. 3A-I are prior art example projection OCT fundus images generated from 3-D OCT images.
Figure 3B:
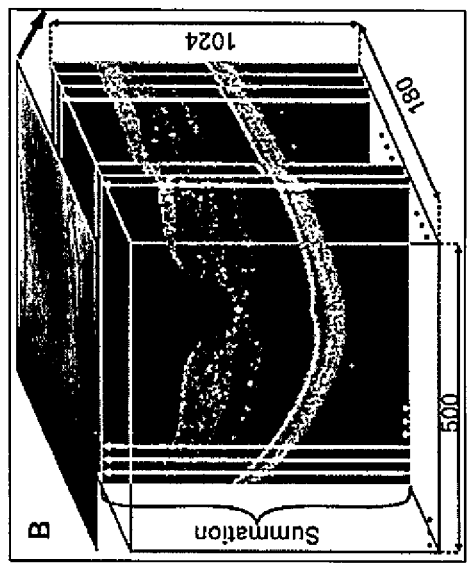
Figure 3A:
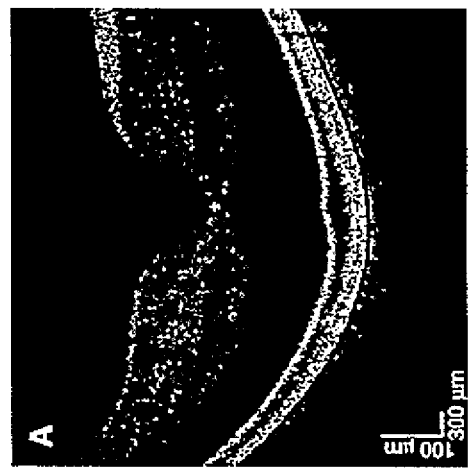
Figure 3F:
Figure 3E:
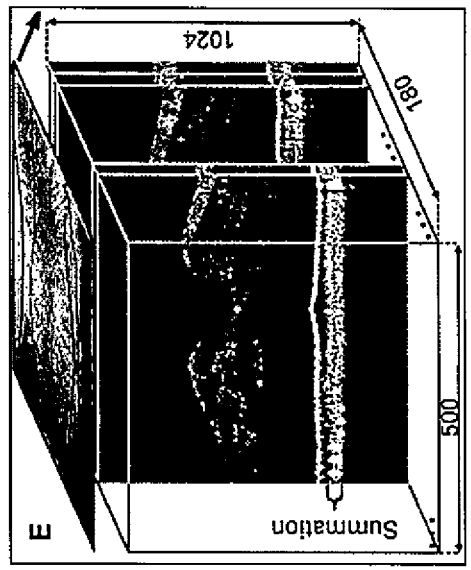
Figure 3D:
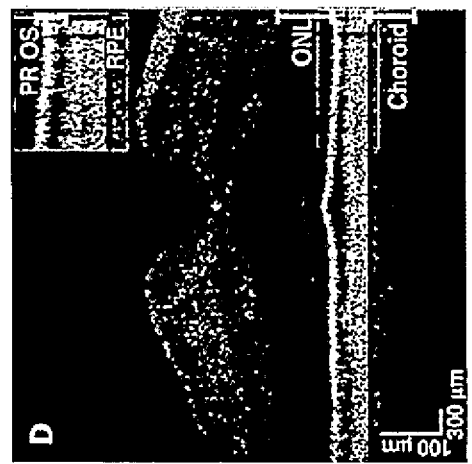
Figure 3I:
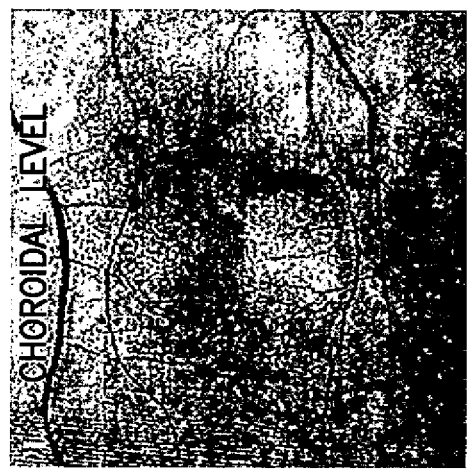
Figure 3H:
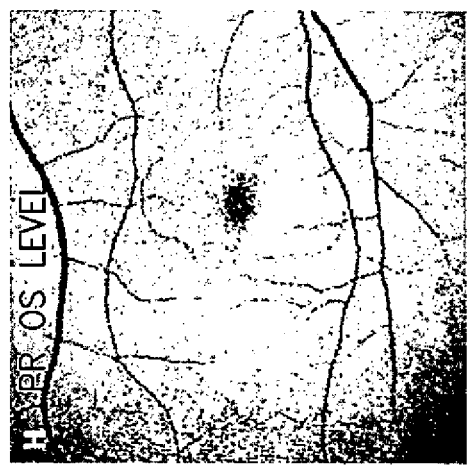
Figure 3G:
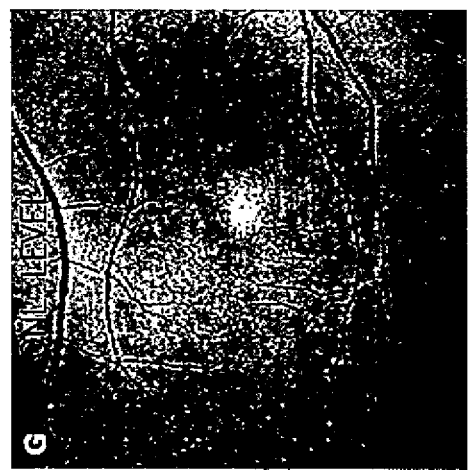

FIGS. 3A-I show prior art examples of such projection OCT fundus images in a normal eye. Specifically, FIG. 3A is a B-scan of an OCT image showing the approximation of the outer retinal contour with fourth-order polynomial curve fit; FIG. 3B is a stack of B-scan OCT images of size 500×1024×180; and FIG. 3C is an OCT fundus image of size 500×180 that is generated by taking the summation of the intensity values of each raw in each B-scan OCT image. FIG. 3D illustrates the manual segmentation of retinal pigment epithelium (RPE) layer (which is marked by the straight line indicated by the arrow); summation of the intensity value of each column of each B-scan in the particular depth of FIG. 3D is shown at FIG. 3E, which results in the OCT projection image of the RPE layer shown at FIG. 3F. The OCT projection image of the optic nuclear layer (ONL) layer shown at FIG. 3G, and of the photoreceptor outer segment (PR-OS) layer shown at FIG. 3H, and of the Choroidal layer shown at FIG. 3I, are all obtained by following the same approach.

Projection OCT fundus imaging facilitates the enhanced visualization of the retinal pathologies related to AMD in the various retinal layers. Different types of drusens exhibit distinct features in projection OCT images. For instance, photo receptor disruption is indicated by loss of the photoreceptor inner/outer segment (IS/OS) boundary and external limiting membrane (ELM). Retinal pigment epithelium (RPE) atrophy can be assessed using choroid-level projection OCT image. These examples make clear that projection OCT imaging is very useful for the early prediction of AMD.

Figure 4B:
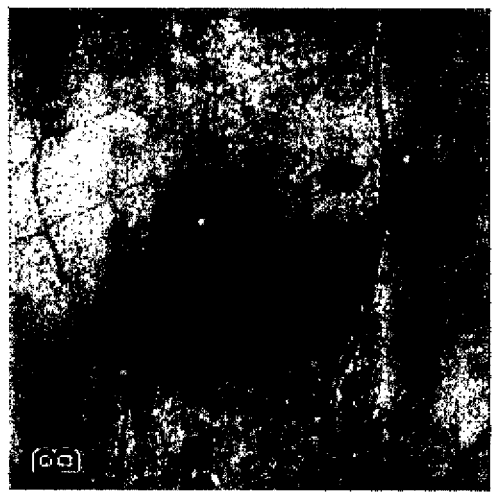
FIGS. 4A-H are images showing the response of retinal fundus image, OCT fundus image and projection OCT fundus images in presence of predominantly hard drusen.
Figure 4A:
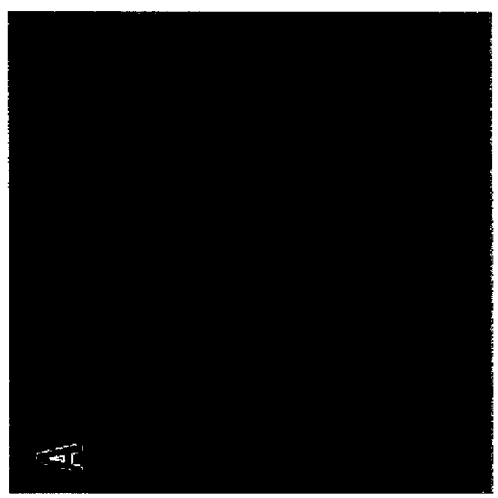
Figure 4D:
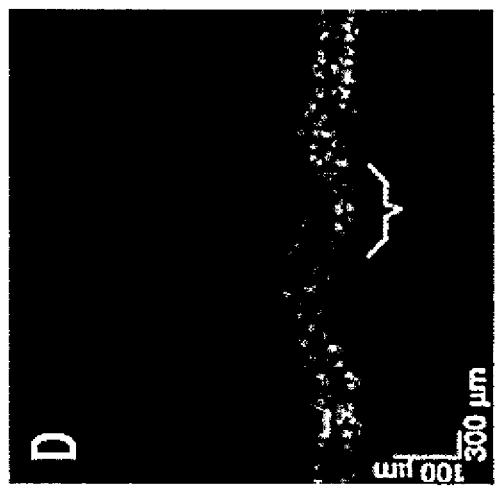
Figure 4C:
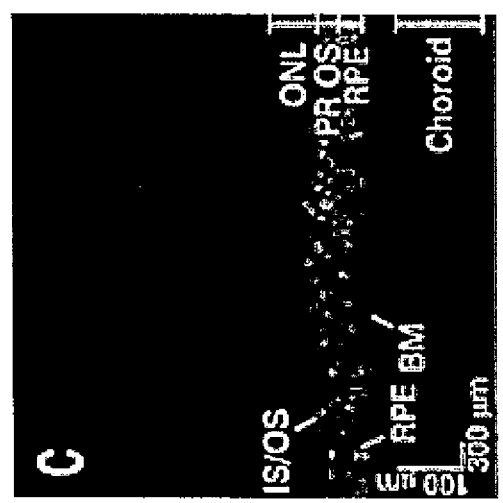
Figure 4F:
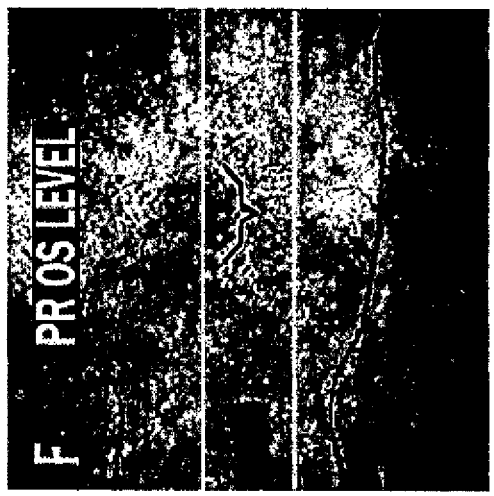
Figure 4E:
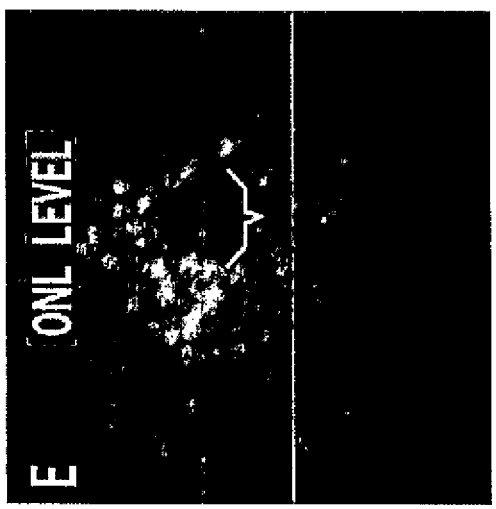
Figure 4H:
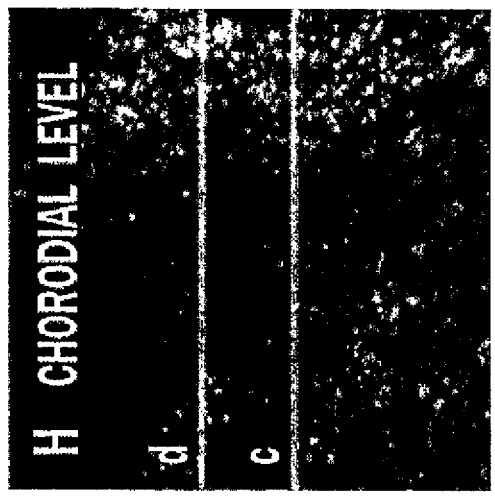
Figure 4G:

FIGS. 4A-H are images showing the response of retinal fundus image, OCT fundus image and projection OCT fundus images in presence of predominantly hard drusen. FIG. 4A is a color fundus photograph and FIG. 4B is an OCT fundus image. FIGS. 4C and 4D are cross-sectional OCT images extracted from the 3-D dataset. FIGS. 4E through 4H are projection OCT fundus images. The brackets in FIGS. 4D and 4F indicate areas of photoreceptor layer disruption. The locations of cross-sectional OCT images at FIGS. 4C-4D are shown as lines on the projection OCT fundus images. In FIG. 4 the acronyms BM represents bruch membrane; ELM is the external limiting membrane; IS/OS is the photoreceptor inner/outer segment junction; ONL is the outer nuclear layer; PR OS is the photoreceptor outer segment; and RPE is the retinal pigment epithelium.

As noted in the background section, projection OCT images require very expensive ultra-high resolution OCT images which at the present time are not widely available. As a consequence, the utilization of projection OCT images in the early prediction of AMD is still very limited. The disclosure herein presents how to estimate projection OCT images from relatively inexpensive and easily available retinal fundus images. It is from these estimated projection OCT images that each represent different biological layers of the patient's eye that AMD predictions can be made with accuracy. But these estimated projection OCT images are created from retinal fundus images of the patient, and not from OCT imaging equipment. As will be detailed below, the described model to do so will provide more detailed information about the AMD pathologies with respect to clinically important retinal tissue layers.

Further, the combination of estimated OCT projection image and retinal fundus image can be used to train a machine learning pipeline for the early prediction of AMD. In this regard a deep convolutional neural network based auto-encoder, similar to the principles outlined in a paper by Gregor, Karol, et al. (see the reference listing at the background section), are directly applicable for the generation of an OCT projection image from the retinal fundus image. To the inventors' knowledge, no previous work has been done on the modelling/reconstruction of an OCT projection image using a retinal fundus image.

The following terminology is employed to more clearly describe the techniques herein, understanding there are separate processes for developing an OCT estimation model that generates estimated OCT images from a retinal fundus image and for using that OCT estimation model within a larger software framework (the AMD prediction model) to predict AMD in an actual patient (whether human or animal). The AMD prediction model, once developed, may be considered as a computer program stored on a computer readable memory that may be distributed for widespread use, including to rural and remote areas where OCT imaging equipment is not readily available or is cost prohibitive. An input retinal fundus image is input to develop the OCT estimation model, while a patient retinal fundus image is input to the developed AMD prediction model for the purpose of predicting AMD in that particular patient. In developing/training the OCT estimation model the input retinal fundus image is matched against actual OCT projection images so that the OCT estimation model will be able to generate/create estimated OCT projection images for multiple biological layers of the eye (or more particularly the retina). Estimated OCT projection images are 2D images that, unlike the actual OCT projection images used to develop the OCT estimation model, do not originate from OCT imaging equipment. When developing the OCT estimation model, features are extracted from the actual OCT projection images (first set of features) and from the input retinal fundus images (second set of features) to perform this matching; a similar feature extraction and matching between the patient retinal fundus image and the estimated OCT projection images generated from it is also employed when putting the AMD prediction model into use. Certain features in one or more biological layers of the actual OCT projection images and how these features change over time (for example, an x % increase in the number of drusens at layers A and D within 3 months) are known to be accurate predictors of AMD, and the OCT estimation model incorporates this AMD prediction knowledge into how it generates the estimated OCT projection images from a given retinal fundus image.

Once the OCT estimation model is developed, we, can input a test retinal fundus image and generate from it the estimated OCT projection images in order to train a machine learning pipeline for the early prediction of AMD. In an embodiment the estimated OCT projection images will be generated by using the correlation of the changes in the retinal fundus and different types of OCT projection images using training data driven stacked convolutional auto-encoders. In this regard it will contain more detailed information as compared to the patient (or test) retinal fundus images that are used to create the estimated OCT projection images.

In this manner we can enhance the feature space of AMD prediction using the combination of estimated OCT projection image and the patient retinal fundus image. When developing the OCT estimation model that generates the estimated OCT projection images, these estimated OCT images can be used only for the training of the auto-encoders of each different-layer OCT projection image, and so in the test or initial training phase of the AMD prediction software only retinal fundus images are needed for the estimation of OCT projection images. Because of this aspect the AMD prediction invention described herein can be made readily available for use in rural and other areas/regions where OCT imaging technology/equipment is not available.

This enables us to leverage the correlation of the changes in the retinal fundus image and different estimated OCT projection images (which are learned by using the big training data driven deep convolutional auto-encoders) for early prediction of AMD. Use of retinal fundus images for the prediction of AMD via estimated OCT images is itself more economical, more affordable and more easily accessible (at least in rural and remote areas) than using actual OCT images to predict AMD. It is not known that training driven prior knowledge of the correlation of the changes of different types of estimated OCT projection image and retinal fundus image has ever before been used for the early prediction of AMD.

Figure 5:
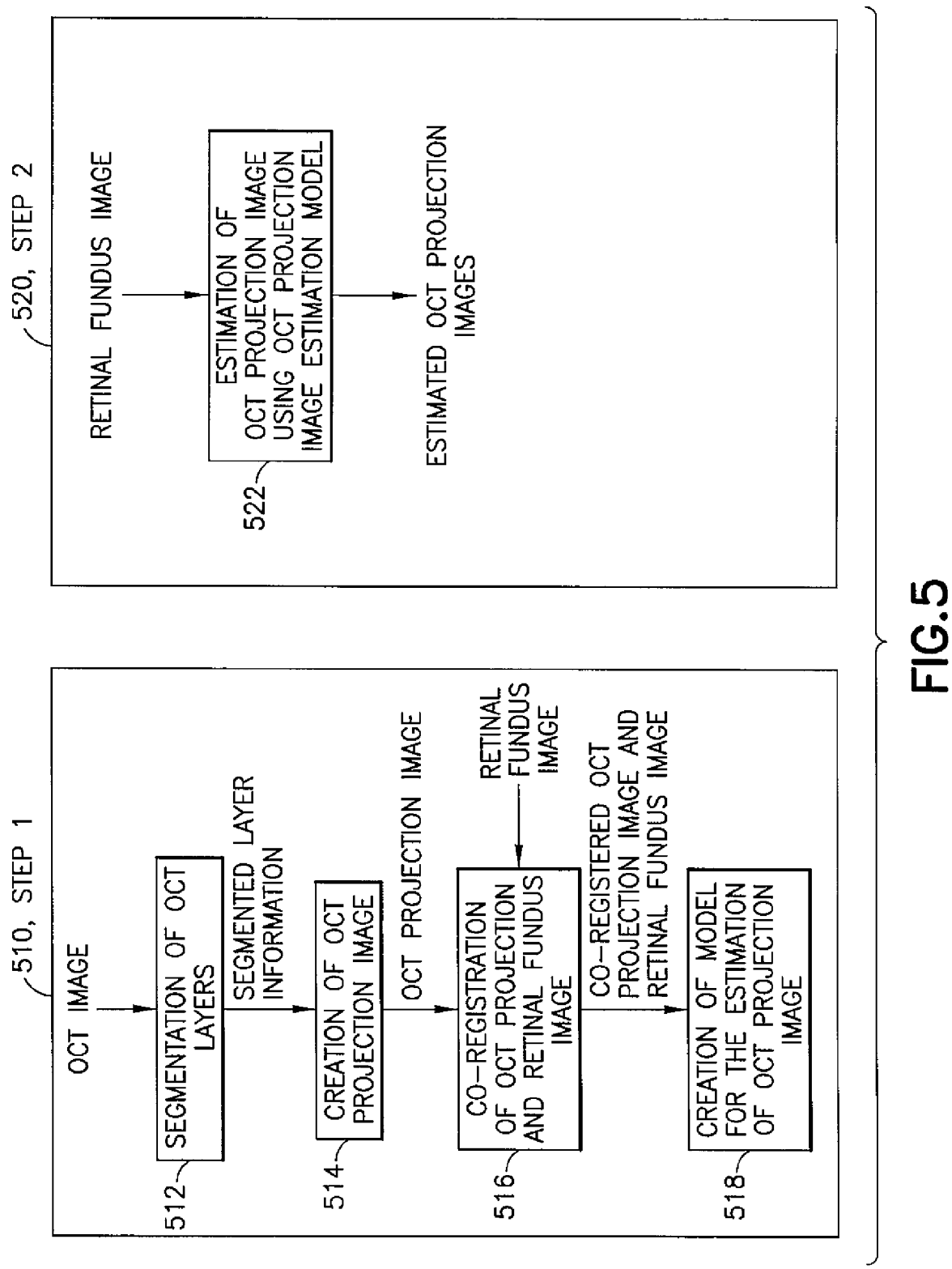
FIG. 5 is a process flow diagram illustrating major steps for estimating of an OCT projection image according to an embodiment of these teachings.

In an example embodiment there are two broad steps concerning the OCT estimation model that generates estimated OCT projection images. In the first step the correlation of the changes in retinal fundus images and different types of actual OCT projection images are modelled so we can know how to generate useful estimated OCT projection images from a given color retinal fundus image; FIG. 5 shows this first step 510 for one biological layer and this is how the OCT estimation model is created. Following that, the OCT estimation model is put within the larger AMD prediction model where it generates different types of estimated OCT projection images from a (test or patient) retinal fundus image, without using actual OCT images. This is shown in FIG. 5 as the second step 520. In the larger AMD prediction model the test retinal fundus image and the estimated OCT projection images generated from it are combined to train a machine learning pipeline for the early prediction of AMD.

Beginning with the first step 510, first the retinal tissue layers in an actual OCT image are segmented 512 and from these layers is generated a corresponding (actual) OCT projection image 514. These are actual OCT images taken with OCT imaging equipment. Next, each OCT projection image is co-registered with the input retinal fundus image 516. In the prior art multi-focal image based AMD prediction a patient's retinal fundus image and that same patient's actual OCT image were compared in order to predict AMD, and so there are libraries of data points relating both of these to the accurate prediction of AMD. When building the OCT estimation model at step 510 it is useful to utilize these retinal fundus images and actual OCT images from the same patient to achieve a more precise and accurate registration of one image to the other, though this is not necessary to the broader teachings herein. Following that the co-registered retinal fundus image and OCT projection images are used to create the OCT estimation model 518 for estimating an OCT projection image. Strictly from the perspective of understanding the invention it may be convenient to consider there may be a different OCT estimation sub-model for generating an estimated OCT projection image for each different biological/tissue layer, and the multiple sub-models together form the OCT estimation model 518 that generates estimated OCT projection images for the different layers from a single patient retinal fundus image at step 520. In a particular example this OCT estimation model is created by training a convolutional neural network based auto-encoder to reconstruct an OCT projection image from a given retinal fundus image. These are detailed more particularly below.

The second step 520 may also be used for testing the OCT estimation model 518 before widespread deployment in the larger AMD prediction model, a test retinal image is passed through the trained auto-encoders that each produce the different-layer estimated OCT projection image 522 which can then be compared against actual OCT projection images associated with the test retinal fundus image to train the system how to generate accurate estimated OCT projection images.

Figure 6:
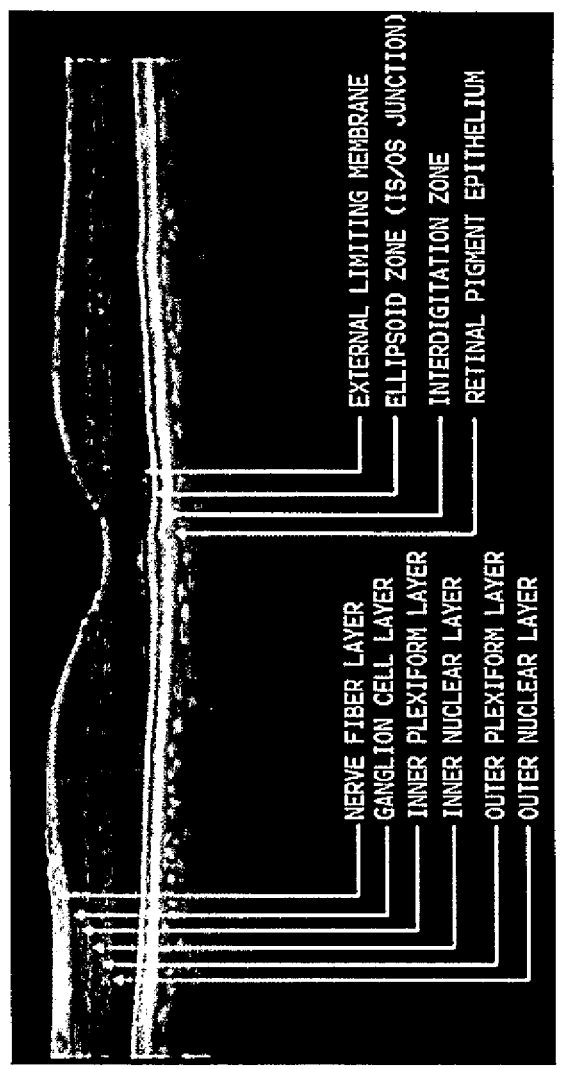
FIG. 6 is an image showing OCT layers that are segmented according to embodiments of these teachings.

There are a number of ways to implement the automatic segmentation of OCT layers 512 in the first step 510. FIG. 6 illustrates some example OCT layers. In the prior art primarily edge mapping and intensity clustering are used for the segmentation of OCT layers, and these non-limiting examples are suitable for embodiments of these teachings also.

As noted above, a 3-dimensional OCT image is segmented 512 to generate the actual projection OCT fundus images 514 of the first step 510. FIGS. 3A-I are prior art example projection OCT fundus images generated in this manner. In an embodiment these (actual) projection OCT fundus images are created by selectively summing different segmented retinal layers (see for example FIG. 3C). It is these automatically segmented OCT layers 512 that are used to generate the OCT projection image 514 for different retinal layers in an embodiment of these teachings.

Figure 7:
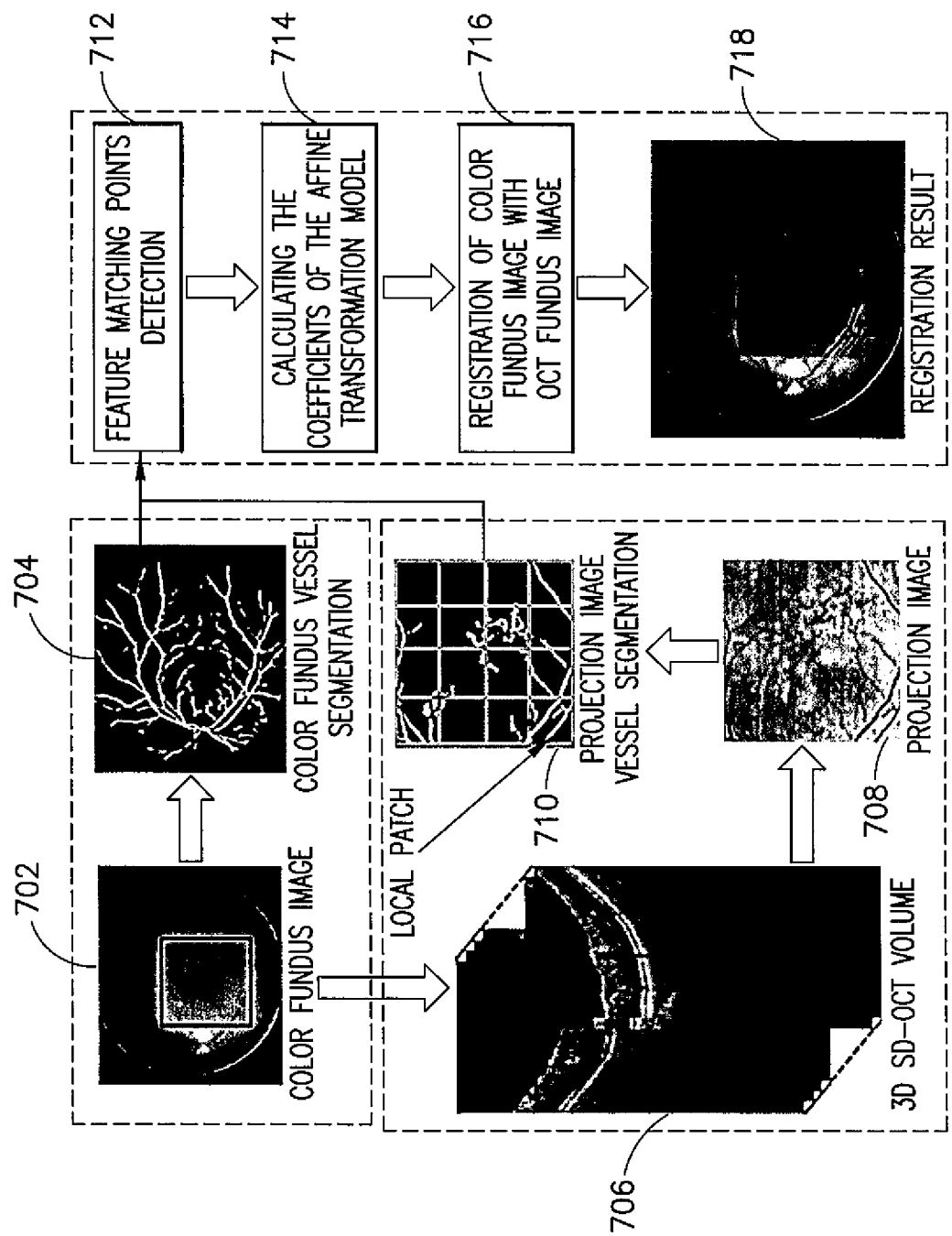
FIG. 7 is a process flow diagram illustrating co-registering of an OCT projection and a retinal fundus image according to an embodiment of these teachings to generate an estimated OCT projection image.

Each different-layer OCT projection image is co-registered 516 with the input retinal fundus image for example using vessel based landmark points. FIG. 7 illustrates some of the major process steps to do so. The input color retinal fundus image is input at 702 and image 704 represents a segmentation of that image that is to match the tissue layer for this model/biological layer. But in fact the color fundus image 702 is only 2D to begin with and so this is not a true segmentation 704 as is done with the 3D OCT image; image 704 represents extracting from the color fundus image only those features relevant to the layer currently being processed. In the FIG. 7 example it is the blood vessel layer but in practice features relevant to the other layers can be extracted from the 2D color fundus image 702 to build the models for those other layers. In the end the same color retinal fundus image has different features extracted for different layers and the process of FIG. 7 repeated for these different layers so there is a model to estimate OCT projection images for each such layer. All of these features extracted from the color retinal fundus image may be considered a first set. If we extract a second set of features from each different layer of the actual OCT projection images, then when matching images only some features of the first set will correspond to features in the layer-specific second set since the first set will have features from the retinal fundus image for all the layers to be matched.

The 3D OCT image (volume) 706 is input and a projection OCT fundus image 708f or the particular layer being processed is generated from that volume. Above are described prior art methods to do this segmentation. Preferably there is a known correspondence between this 3D OCT image and the input retina fundus image 702, such as being from the same historical patient as noted above. The vessel layer is the example layer being processed in FIG. 7 and so the projection OCT fundus image 708 for this layer is segmented at 710 where the second set of features are extracted. The segmented color retinal fundus image 704 and the segmented projection OCT fundus image 710 for the same tissue layer are then compared to find the matching feature points at 712. A calculation is done to correlate these two images at 714 using feature matching, for example by computing coefficients of an affine transformation model. With this fitted correlation model (518 in FIG. 5) the color retinal fundus image 702 is registered with the OCT projection fundus image 706, and from the result 718 we will know how to estimate an OCT projection image (for that tissue/biological layer) using only a given retinal fundus image. The feature matching at 714 can emphasize those features that are already known to be accurate predictors of AMD.

The quality of OCT estimation model created at 518 of FIG. 5 is an important aspect to obtaining high accuracy in AMD prediction from retinal fundus images 702. In an embodiment the OCT estimation model 518 utilizes a deep convolutional neural network based image reconstruction approach (for example, an auto-encoder) to model the correlation in the changes of a retinal fundus image and actual OCT projection images of different tissue layers. So for example if we build the OCT estimation model 518 using an input retinal fundus image and a 3D OCT volume taken from a given historical patient in May 2005, and also using an input retinal fundus image and a 3D OCT volume taken from that same historical patient in May 2006, the OCT estimation model 518 can better identify which features that changed over time in those two color fundus images would be most relevant to predicting AMD in that patient, and weight them appropriately. This is possible because accurate AMD prediction in the prior art lies in the OCT projection image layers, more specifically the number, count and location of drusens in a given layer and in combinations of layers (among other predictors).

In general we may consider a (single layer) auto-encoder as a neural network that has three computational layers (different from the tissue/biological layers discussed herein): an input layer, a hidden (encoding) layer, and a decoding layer. The network is trained to reconstruct its inputs, which forces the hidden layer to try to learn good representations of those inputs. In order to encourage the hidden layer to learn good input representations, there are certain variations on the simple auto-encoder such as de-noising auto-encoders and contractive auto-encoders which are respectively discussed in detail at the (first-listed) Masci reference and the Vincent reference listed in the background section. The preferred approach for these teachings is for the OCT estimation model 518 to utilize a convolution auto-encoder for modelling the transformation from retinal fundus image to OCT projection image at multiple levels. The Rifai reference listed in the background section provides further detail on convolution auto-encoding, and this technique is preferred for the purposes herein because the convolution auto-encoder takes into account contextual information for image reconstruction.

Convolutional auto-encoders are the adaptation of auto-encoders to images (or other spatially-structured data). They are typically built with convolutional layers where each layer consists of a number of feature maps. Each feature map is produced by convolving a small filter with the layer's inputs; adding a bias, and then applying some non-linear activation function. Additionally, a maximum-pooling operation can be performed on each feature map by dividing it into small non-overlapping regions and taking the maximum over each region. Maximum-pooling down-samples the latent representation by a constant factor, usually taking the maximum value over non overlapping sub-regions. This helps improve the filter selectivity, because activation of each neuron in the latent representation is determined by the "match" between the feature and the input field over the region of interest.

Figure 8:
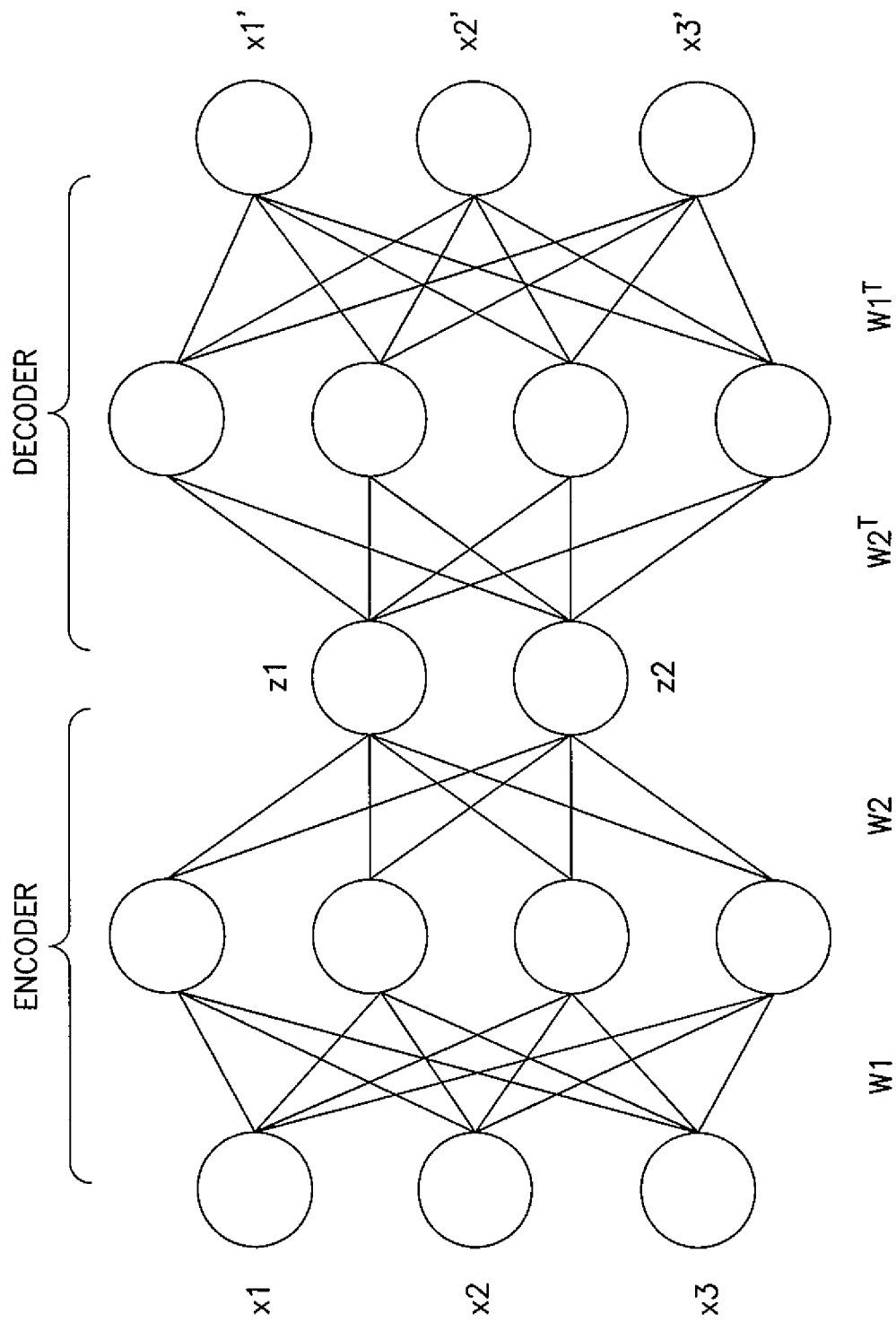
FIG. 8 is a conceptual view of an auto-encoder having an equal number of nodes in the input layer and in the output layer, which can be used to create the model for estimating OCT projection images according to an embodiment of these teachings.

FIG. 8 is a conceptual view of an auto-encoder having an equal number of nodes in the input layer and in the output layer. The input nodes are {X1, X2, X3}, the output nodes are {X1', X2', X3'}, and the hidden layer is represented as nodes {Z1, Z2} between the encoder and decoder layers. In one embodiment we create the model for estimating OCT projection images by stacking several auto encoders to form a deep hierarchy. Further detail on stacking convolutional auto-encoders can be seen at the second-listed Masci reference detailed in the background section. Stacking several auto-encoders such that each layer of the stack receives its input from the latent representation of the layer below forms a deep hierarchy. For deep belief networks, unsupervised pre-training can be done in greedy, layer-wise fashion and the weights can be fine-tuned afterwards using back-propagation.

Figure 9:
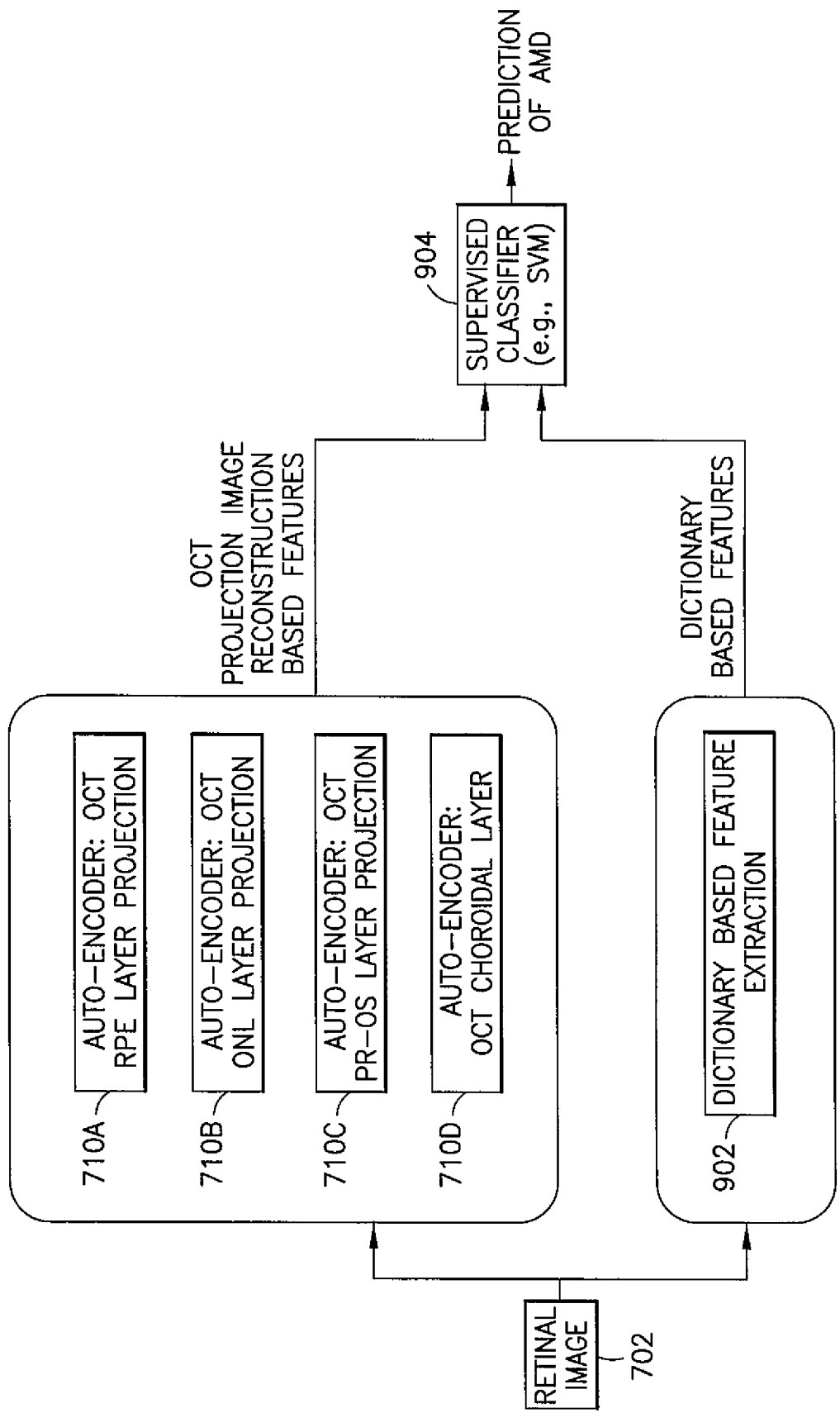
FIG. 9 is a block diagram of the OCT projection image reconstruction based AMD prediction model.

One important goal of these teaching is to facilitate the accurate and early prediction of AMD, and FIG. 9 is a block diagram of the OCT projection image reconstruction based AMD prediction model showing further details in addition to those described above. Whereas FIGS. 5 and 7 described how to build the OCT estimation model that generates the estimated OCT projection images from a given retinal fundus image, FIG. 9 describes how the larger AMD prediction model can utilize it in practice. FIG. 9 uses the characteristics of a reconstructed/estimated OCT projection images which are generated for multiple biological/tissue layers using the OCT estimation model described at FIGS. 5 and 7. Because FIG. 9 operates with multiple layers, the auto-encoder (or stack of auto-encoders) may in this example trained for the OCT projection image of the retinal pigment epithelium layer (RPE) 710A, and for the OCT projection image of the outer nuclear layer (ONL) 710B, and for the OCT projection image of the photoreceptor outer segment layer (PR-OS) 710C and for the OCT projection image of the choroidal layer 710D. In FIG. 9 the AMD prediction model takes the patient's retinal fundus image 702 in the input layer and corresponding estimated OCT projection images generated by the OCT estimation model are output in the output layer.

In the test phase, the test retinal fundus image 702 will be pass through each of these stacked auto-encoders as shown by example at FIG. 9, and the top level activations of each auto-encoder will be extracted as the OCT projection image reconstruction based feature. These represent the estimated OCT projection images. In addition to that, the FIG. 9 example includes state of the art dictionary based features 902 from the retinal fundus image 702. The combination of OCT projection image reconstruction based feature 710A-D (the estimated OCT projection images) and the dictionary based features 902 will be used in a supervised classifier 904 to predict the severity of AMD (quantitatively). The supervised classifier 904 may be implemented for example as a support vector machine (SVM) or as a random forest (RF).

Figure 10:
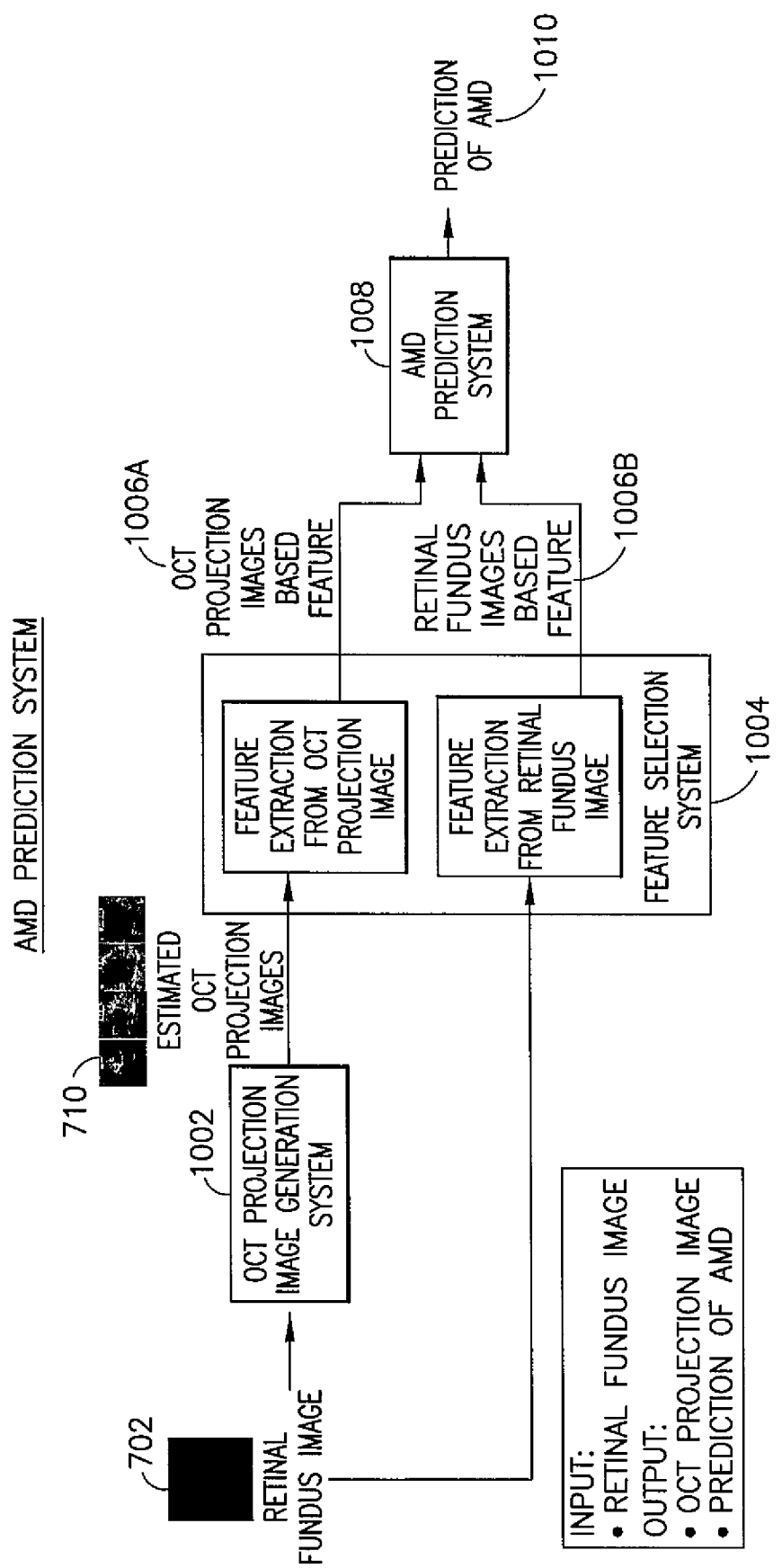
FIG. 10 shows a more generalized view of FIG. 9 with a patient's retinal fundus image as the only input to the AMD prediction system/program that utilizes the OCT projection image estimating models created at FIGS. 5 and 7.

FIG. 10 shows a more generalized view of the AMD prediction model of FIG. 9. All the OCT projection images in FIG. 10 are generated from the patient retinal fundus image that is an input to the system and so are estimated OCT projection images. If we consider the group of per-biological/tissue layer models developed according to FIGS. 5 and 7 as a computer program or other type of OCT projection image generation system 1002, then FIG. 10 illustrates how that program/system is put into use, first by generating estimated OCT projection images 710 for the multiple biological layers from a patient's retinal fundus image 702. A feature selection system 1004 extracts a first set of features 1006A from each of the estimated OCT projection images 710, and further extracts a second set of features from the patient's retinal fundus image 702. The AMD prediction system 1008 takes these feature set 1006A/B inputs and evaluates them in the context of one another to predict 1010 AMD in the patient.

A particularly elegant aspect of these teachings is that the model to generate the estimated OCT projection images uses the prior knowledge (learned from the training data) of the correlation of the changes in different OCT projection image with the changes to retinal fundus images for the prediction of AMD. To the inventors' knowledge this has never been done before.

Figure 11:
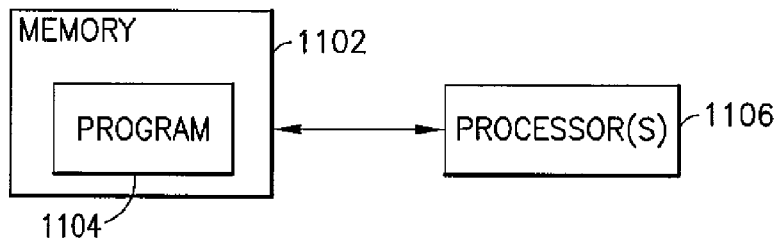
FIG. 11 is a high level block diagram showing a computing system for performing functions according to these teachings.

FIG. 11 illustrates some components of a system for implementing certain aspects of these teachings. There is one or more computer readable memories 1102 storing one or more computer executable programs 1104 that are executable by one or more processors 1106 that may implement the stacked auto-encoders described above.

Figure 12:
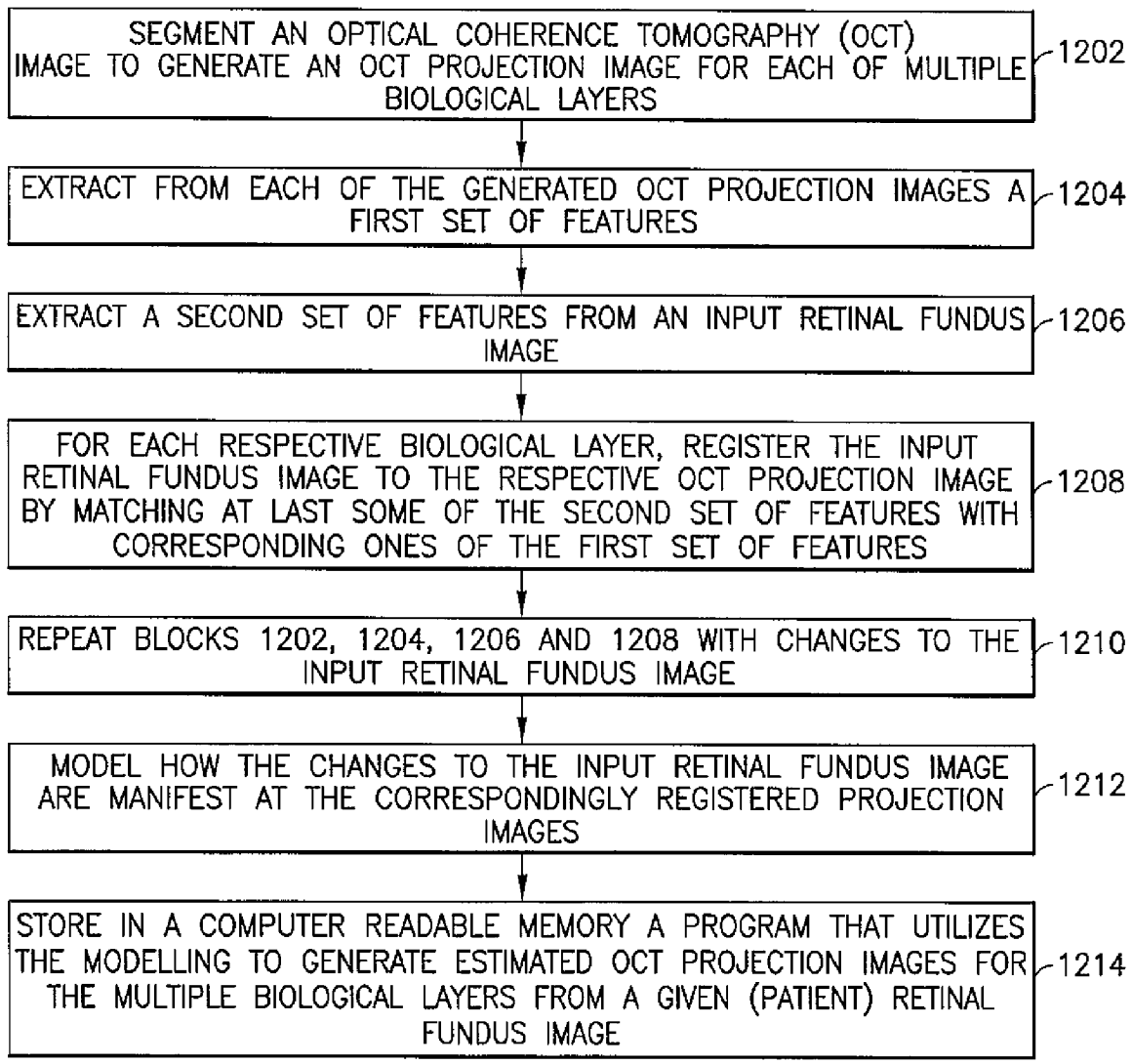
FIG. 12 is a logic flow diagram illustrating a method that encompasses certain features of the embodiments of this invention.

FIG. 12 is a process flow diagram describing certain of the above-described steps for creating the program that generates the estimated OCT projection images from only a 2D color retinal fundus image. At block 1202 an optical coherence tomography (OCT) image is segmented to generate an OCT projection image for each of multiple biological/tissue layers and at block 1204 a first set of features is extracting from each of the generated OCT projection images. Separately at block 1206 a second set of features is extracted from an input retinal fundus image. Block 1208 has, for each respective biological layer, the registration of the input retinal fundus image to the respective OCT projection image and this is done by matching at least some of the second set of features with corresponding ones of the first set of features. Blocks 102, 1204, 1206 and 1208 are repeated at block 1210 with changes to the input retinal fundus image. Modelling how the changes to the input retinal fundus image are manifest at the correspondingly registered projection images is done at block 1212, and at block 1214 the computer program is generated and stored in a computer readable memory; this program utilizes the modelling of block 1212 to generate estimated OCT projection images for the multiple biological layers from any given retinal fundus image such as a test retinal fundal image (if the modelling is to further fine-tuned) or a patient's retinal fundus image.

The present invention may be implemented as a system, a method, and/or a computer program product. The computer program product may include a computer readable storage medium (or media) having computer readable program instructions stored thereon for causing a processor to carry out certain aspects of the present invention.

The computer readable storage medium such as the memory 1102 can be a tangible device that can retain and store instructions for use by an instruction execution device (such as the data processor(s) 1106 of the computer shown at FIG. 11). The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or, entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

As such, various modifications and adaptations may become apparent to those skilled in the relevant arts in view of the foregoing description, when read in conjunction with the accompanying drawings and the appended claims. As but some examples, the use of other similar or equivalent vulnerability types may be used by those skilled in the art. However, all such and similar modifications of the teachings of this invention will still fall within the scope of this invention.

What is claimed is:

1. A method comprising:
a) segmenting an optical coherence tomography (OCT) image to generate an OCT projection image for each of multiple biological layers;
b) extracting from each of the generated OCT projection images a first set of features;
c) extracting a second set of features from an input retinal fundus image;
d) for each respective biological layer, registering the input retinal fundus image to the respective OCT projection image by matching at least some of the second set of features with corresponding ones of the first set of features;
e) repeating elements a) through d) with changes to the input retinal fundus image;
f) modelling how the changes to the input retinal fundus image are manifest at the correspondingly registered projection images; and
g) storing in a computer readable memory a program that utilizes the modelling to generate estimated OCT projection images for the multiple biological layers from a given retinal fundus image.

2. The method according to claim 1, further comprising:
using the stored program to generate estimated OCT projection images for the multiple biological layers from a patient's retinal fundus image;
extracting from each of the estimated OCT projection images a first set of features;
extracting a second set of features from the patient's retinal fundus image; and
evaluating the first set of features extracted from each of the estimated OCT projection images in combination with the second set of features extracted from the patient's retinal fundus image to predict age related macular degeneration (AMD) in the patient.

3. The method according to claim 2, wherein the stored program is used to predict AMD in the patient in the absence of inputting to the program any OCT images of the patient.

4. The method according to claim 1, wherein each of the estimated OCT projection images are generated by an auto-encoder.

5. The method according to claim 4, wherein there are a plurality of convolution auto-encoders in a stacked arrangement, each of the auto-encoders configured to generate from each of the input retinal fundus images the estimated OCT projection image for only one of the biological layers.

6. The method according to claim 1, wherein each of the first and second sets of features comprise vessel based landmark points.

7. The method according to claim 1, wherein at least some of the changes to the input retinal fundus image are manifest at the correspondingly registered projection images as changes to size, number and/or location of drusen.

8. A computer readable memory storing an executable program comprising:
   a) code to segment an optical coherence tomography (OCT) image to generate an OCT projection image for each of multiple biological layers;
   b) code to extract from each of the generated OCT projection images a first set of features;
   c) code to extract a second set of features from an input retinal fundus image;
   d) code to register the input retinal fundus image to the respective OCT projection images of each respective biological layer by matching at least some of the second set of features with corresponding ones of the first set of features;
   e) code to repeat elements a) through d) with changes to the input retinal fundus image;
   f) code to model how the changes to the input retinal fundus image are manifest at the correspondingly registered projection images; and
   g) code to utilize the model for generating estimated OCT projection images for the multiple biological layers from a given retinal fundus image.

9. The method according to claim 1, the executable program further comprising:
   code to extract from each of the generated estimated OCT projection images a first set of features;
   code to extract a second set of features from the given retinal fundus image; and
   code to evaluate the first set of features extracted from each of the estimated OCT projection images in combination with the second set of features extracted from the given retinal fundus image to predict age related macular degeneration (AMD) from the given retinal fundus image.

10. The computer readable memory according to claim 9, wherein the code to evaluate and to predict AMD operates in the absence of any actual OCT images being input to the executable program after the changes are modelled.

11. The computer readable memory according to claim 9, wherein the model comprises an auto-encoder.

12. The computer readable memory according to claim 11, wherein the model comprises a plurality of convolution auto-encoders in a stacked arrangement, each of the auto-encoders configured to generate from each of the input retinal fundus images the estimated OCT projection image for only one of the biological layers.

13. The computer readable memory according to claim 9, wherein each of the first and second sets of features comprise vessel based landmark points.

14. The computer readable memory according to claim 9, wherein at least some of the changes to the input retinal fundus image are manifest at the correspondingly registered projection images as changes to size, number and/or location of drusens.

15. An apparatus comprising:
   one or more memories comprising computer-readable code and one or more processors, wherein the one or more processors are configured, in response to execution of the computer-readable code, to cause the apparatus to perform actions comprising:
   a) segmenting an optical coherence tomography (OCT) image to generate an OCT projection image for each of multiple biological layers;
   b) extracting from each of the generated OCT projection images a first set of features;
   c) extracting a second set of features from an input retinal fundus image;
   d) for each respective biological layer, registering the input retinal fundus image to the respective OCT projection image by matching at least some of the second set of features with corresponding ones of the first set of features;
   e) repeating elements a) through d) with changes to the input retinal fundus image;
   f) modelling how the changes to the input retinal fundus image are manifest at the correspondingly registered projection images; and
   g) storing in the one or more memories a program that utilizes the modelling to generate estimated OCT projection images for the multiple biological layers from a given retinal fundus image.

16. The apparatus according to claim 15, the actions further comprising:
   using the stored program to generate estimated OCT projection images for the multiple biological layers from a patient's retinal fundus image;
   extracting from each of the estimated OCT projection images a first set of features;
   extracting a second set of features from the patient's retinal fundus image; and
   evaluating the first set of features extracted from each of the estimated OCT projection images in combination with the second set of features extracted from the patient's retinal fundus image to predict age related macular degeneration (AMD) in the patient.

17. The apparatus according to claim 16, wherein the stored program is used to predict AMD in the patient in the absence of inputting to the program any OCT images of the patient.

18. The apparatus according to claim 15, wherein each of the estimated OCT projection images are generated by an auto-encoder.

19. The apparatus according to claim 18, wherein there are a plurality of convolution auto-encoders in a stacked arrangement, each of the auto-encoders configured to generate from each of the input retinal fundus images the estimated OCT projection image for only one of the biological layers.

20. The apparatus according to claim 15, wherein at least some of the changes to the input retinal fundus image are manifest at the correspondingly registered projection images as changes to size, number and/or location of drusens.

* * * * *